(12) United States Patent
Mitsui

(10) Patent No.: US 11,974,907 B2
(45) Date of Patent: May 7, 2024

(54) PELVIC FLOOR MUSCLE SUPPORTING AID

(71) Applicant: WOMEN'S MEDICAL RESEARCH, INC., Tokyo (JP)

(72) Inventor: Keiko Mitsui, Tokyo (JP)

(73) Assignee: WOMEN'S MEDICAL RESEARCH, INC., Tokyo (JP)

( * ) Notice: Subject to any disclaimer, the term of this patent is extended or adjusted under 35 U.S.C. 154(b) by 566 days.

(21) Appl. No.: 16/650,121

(22) PCT Filed: Sep. 26, 2018

(86) PCT No.: PCT/JP2018/035624
§ 371 (c)(1),
(2) Date: Mar. 24, 2020

(87) PCT Pub. No.: WO2019/065708
PCT Pub. Date: Apr. 4, 2019

(65) Prior Publication Data
US 2020/0276004 A1    Sep. 3, 2020

(30) Foreign Application Priority Data
Sep. 26, 2017 (JP) .................... 2017-185488

(51) Int. Cl.
*A61F 2/00* (2006.01)
*A41B 9/04* (2006.01)
(Continued)

(52) U.S. Cl.
CPC .............. *A61F 2/0009* (2013.01); *A41B 9/04* (2013.01); *A61F 5/24* (2013.01); *A61F 5/37* (2013.01)

(58) Field of Classification Search
CPC ........ A61F 2/00; A61F 2/0004; A61F 2/0009; A61F 2/0031; A61F 2/0045; A61F 2/005;
(Continued)

(56) References Cited

U.S. PATENT DOCUMENTS

| 2,831,486 A * | 4/1958 | Sanders ................ A41B 9/04 |
| | | 604/401 |
| 2008/0032580 A1* | 2/2008 | Fukuoka ................ D04B 1/18 |
| | | 28/103 |
| 2015/0223524 A1* | 8/2015 | Brady ................ A41D 1/089 |
| | | 450/156 |

FOREIGN PATENT DOCUMENTS

| JP | H2-66609 U | 5/1990 |
| JP | 2008-19547 A | 1/2008 |

(Continued)

OTHER PUBLICATIONS

International Search Report dated Dec. 4, 2018 in corresponding International application No. PCT/JP2018/035624; 3 pages.
(Continued)

*Primary Examiner* — Ophelia A Hawthorne
*Assistant Examiner* — Gina McCarthy
(74) *Attorney, Agent, or Firm* — Maier & Maier, PLLC

(57) ABSTRACT

Embodiments are utilized to provide a pelvic floor muscle supporting aid that not only supports the pelvic floor muscles but also is effective for preventing a pelvic organ prolapse. An annular part provided so as to be situated at a position corresponding to an outer peripheral portion of the vaginal opening is pulled by a pulling part, so that an interval between left and right side portions situated on the left and right of the vaginal opening is narrowed. Consequently, not only force to press up the pelvic floor muscles from under is applied but also the vaginal opening is narrowed. Consequently, the pelvic organs do not easily slip out. Therefore, it is possible to prevent urinary incontinence and the like by supporting the pelvic floor muscles and at the same time prevent a pelvic organ prolapse.

5 Claims, 4 Drawing Sheets

(51) Int. Cl.
*A61F 5/24* (2006.01)
*A61F 5/37* (2006.01)

(58) Field of Classification Search
CPC .... A61F 5/00; A61F 5/004; A61F 5/01; A61F 5/02; A61F 5/24; A61F 5/37; A41B 9/00; A41B 9/007; A41B 9/04; A41B 2400/00; A41B 2400/32; A41C 1/00; A41C 1/02; A41C 1/12; A41D 1/089; D04B 1/18
See application file for complete search history.

(56) References Cited

FOREIGN PATENT DOCUMENTS

| | | | |
|---|---|---|---|
| JP | 2008-303518 | A | 12/2008 |
| JP | 2010-144307 | A | 7/2010 |
| JP | 5492339 | B1 | 5/2014 |
| JP | 5661405 | B2 | 1/2015 |
| JP | 2016-94690 | A | 5/2016 |

OTHER PUBLICATIONS

Written Opinion of the International Searching Authority dated Dec. 4, 2018 in corresponding International application No. PCT/JP2018/035624; 3 pages.

\* cited by examiner (a)

(b)

PELVIC FLOOR MUSCLE SUPPORTING AID

FIELD

The present invention relates to a pelvic floor muscle supporting aid that is worn on the crotch and has an aiding function to support the pelvic floor muscles from under.

BACKGROUND

The pelvic floor muscles (a generic name for levator ani muscle (pelvic diaphragm), anococcygeal ligament, deep transverse muscle of the perineum, urethral sphincter, levator ani muscle, and the like, which are also called the pelvic floor muscle group) lie on the bottom of the pelvis and function mainly to support the internal organs, but their function may be weakened by childbirth, aging, and so on. The weakened function of the pelvic floor muscles may cause urinary incontinence, bad posture, motor decline, and so on, and may also lead to a pelvic organ prolapse which is the falling down of the pelvic organs from the normal positions. Therefore, exercises whose aim is to enable a person to learn how to contract the pelvic floor muscles have been recommended. Japanese Patent No. 5661405 discloses a girdle for causing such exercises to be done properly to enhance the effect. This girdle includes extendable belt-shaped structures whose action regions are inner side portions of leg parts of the girdle and which each include a front lifting structure extending from the action region toward a front body and a back lifting structure extending from the action region toward a back body, and they transmit their pulling forces to each other owing to their elasticity. In this girdle, hardly extendable structures that hardly undergo elastic deformation are also formed on the action regions in the leg parts and their vicinity. The elastic force acts on the action regions in the leg parts to contribute to the contraction of the pelvic floor muscles.

Further, Japanese Patent Application Laid-open No. 2016-94690 relates to a supporter whose crotch wear article in a substantially flat plate shape is put on the crotch and is pulled upward with traction strings. This supporter supports the pelvic floor muscles while lifting them up, thereby preventing the function of the pelvic floor muscles from weakening. Japanese Patent No. 5492339 discloses women's underwear intended particularly to curb or prevent a pelvic organ prolapse by combining a stretchable sheet and a low-stretchable sheet.

SUMMARY

A pelvic organ prolapse is a phenomenon that the pelvic organs fall down from the normal position as described above, and owing to the gravity, force that tries to open the vaginal opening and causes the pelvic organs to come out acts. Therefore, only by simply applying, to the female genitals, force in such a direction as to press the pelvic floor muscles upward, it is difficult to prevent the vaginal opening from being opened, and it is not possible, either, to expect a high effect of recovering the function of the pelvic floor muscles. In this respect, in Patent Documents 1 and 2, a portion in contact with the crotch part with which the vagina or the pudendum is in direct contact is pressed upward, whereby the pelvic floor muscles are only pressed upward, and the effects of recovering the function of the pelvic floor muscles and preventing the pelvic organ prolapse cannot be expected much. Patent Document 3 states that the effect of preventing the pelvic organ prolapse is obtained, but the function obtained therein is substantially the same as those obtained in Patent Documents 1 and 2, and only the force pressing the crotch part upward acts. Accordingly, it doesn't seem that high effects of recovering the function of the pelvic floor muscles and preventing the pelvic organ prolapse can be expected.

The present invention was made in consideration of the above-described circumstances, and has an object to provide a pelvic floor muscle supporting aid that can contribute to the functional recovery of the pelvic floor muscles by supporting the pelvic floor muscles, thereby capable of preventing urinary incontinence and the like, and in addition that has a high effect of preventing a pelvic organ prolapse.

To solve the above problem, the present invention includes:

an annular part which is provided so as to be situated at a position corresponding to an outer peripheral portion of a vaginal opening when the pelvic floor muscle supporting aid is worn; and a pulling part which is coupled with the annular part and pulls the annular part in at least a front direction or a back direction of the vaginal opening to narrow an interval between left and right side portions of the annular part, the left and right side portions being situated on left and right of the vaginal opening.

Preferably, the pelvic floor muscle supporting aid further includes a middle pressing part which is between the left and right side portions of the annular part and is pulled by the pulling part.

Further, preferably, the pelvic floor muscle supporting aid is of an underpants type having a front body, a back body, and a crotch part, the annular part is provided in a range including the crotch part, and the pulling part has a front pulling part provided on a range in the front body and a back pulling part provided on a range in the back body.

Preferably, the front pulling part includes a plurality of front pulling parts which are formed to fan out from a front portion of the annular part toward an upper portion of the front body, and the back pulling part has one end connected to a vicinity of a middle portion of a back portion of the annular part and has the other end extending toward an upper portion of the back body.

In this case, preferably, the plurality of the front pulling parts are two front pulling parts which form a substantially V shape, and the single back pulling part is provided along a vicinity of a widthwise middle portion of the back body.

Preferably, at least part of the annular part bulges in a thickness direction. Further preferably, at least part of the middle pressing part bulges in a thickness direction.

Further, the front body and the back body each can be formed of a cloth that does not easily get frayed from a cut edge.

According to the present invention, the annular part provided so as to be situated at the position corresponding to the outer peripheral portion of the vaginal opening is pulled by the pulling part, so that the interval between the left and right side portions situated on the left and right of the vaginal opening is narrowed. Consequently, not only force pressing up the pelvic floor muscles from under is applied but also the vaginal opening is narrowed. Since the pelvic floor muscles are supported by the upward force, it is possible to curb the loosening and damage of the pelvic floor muscles, which is effective for preventing urinary incontinence and the like. Further, since the vagina is supported from under against a pressure applied thereto from above, it is possible to reduce the expansion of the vagina and also prevent the pelvic organs from easily slipping out. That is, according to the pelvic floor muscle supporting aid of the present invention, it is possible not only to prevent urinary incontinence and the like by supporting the pelvic floor muscles but also to prevent the pelvic organ prolapse.

DETAILED DESCRIPTION

Figure 1:
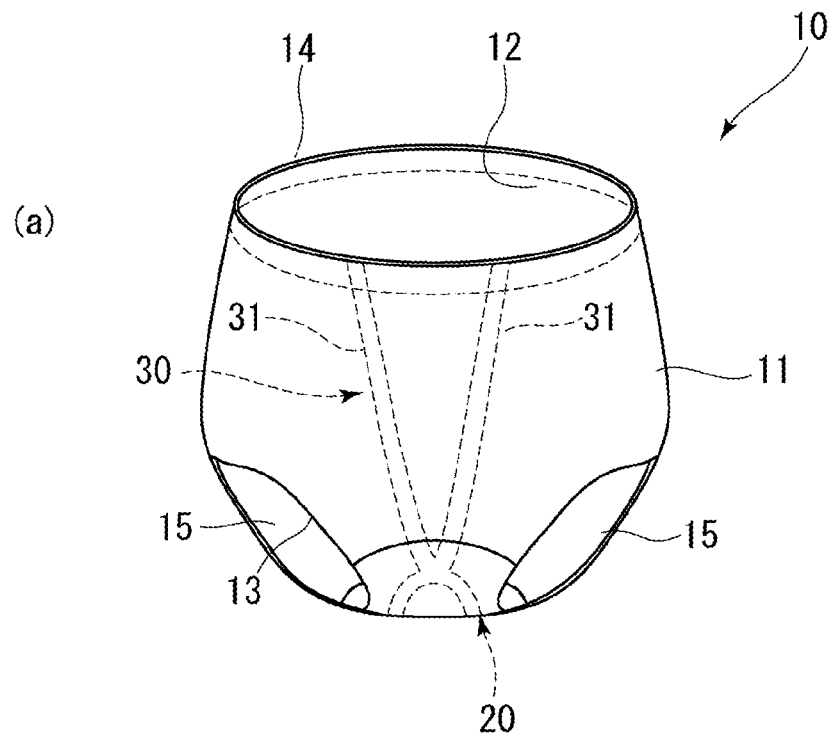
FIG. 1(a) is a perspective view of a pelvic floor muscle supporting aid according to one embodiment of the present invention seen from the front.
FIG. 1(b) is a perspective view thereof seen from the back.
Figure 1:
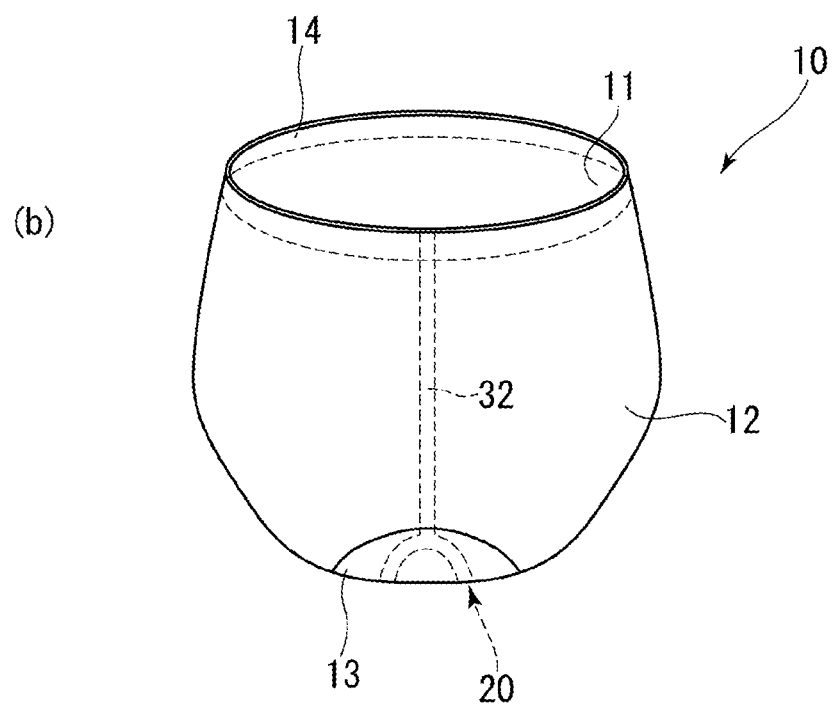
Figure 2:
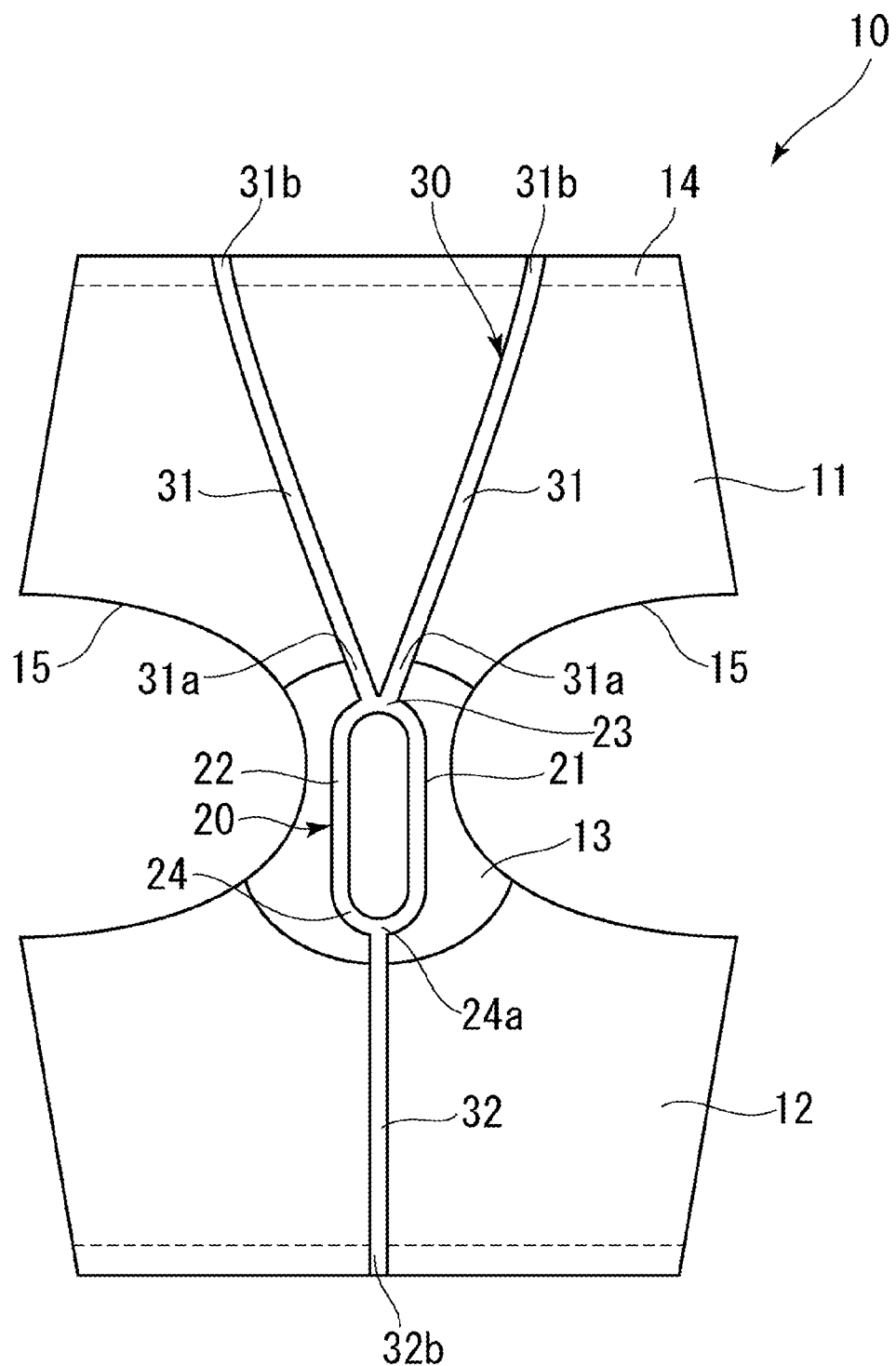
FIG. 2 is a developed view of the pelvic floor muscle supporting aid in FIG. 1.
Figure 3:
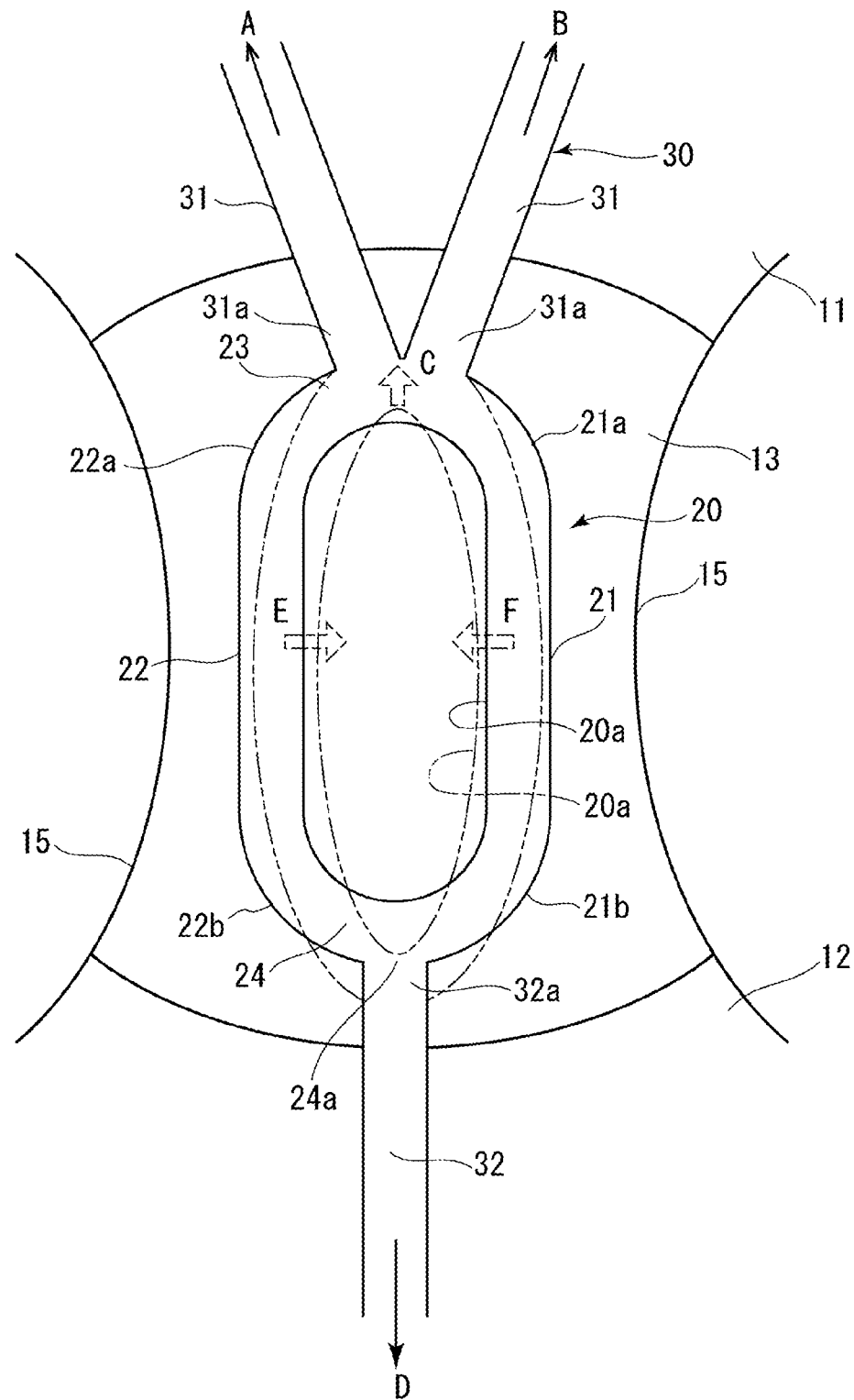
FIG. 3 is an explanatory view of the operation of the pelvic floor muscle supporting aid and is a plan view of its annular part.

The present invention will be hereinafter described in more detail based on embodiments illustrated in the drawings. FIG. 1 to FIG. 3 are views illustrating a pelvic floor muscle supporting aid 10 of this embodiment. As illustrated in these drawings, the pelvic floor muscle supporting aid 10 of this embodiment is of an underpants type and has a front body 11 situated at the front, a back body 12 situated at the back, and a crotch part 13 which is between the front body 11 and the back body 12 and is situated at a position corresponding to the crotch. Inside the crotch part 13, a crotch cloth for making the range of the crotch part 13 double-layered is provided. Note that the meaning of the underpants type mentioned here includes all the types ordinarily used as underwear and correction wear, including not only shorts type with short leg parts but also a type with long leg parts, a sanitary underwear type, and a girdle type. Further, the front body 11, the back body 12, and the crotch part 13 imply positions at which they are situated in the worn state, and the meaning of the underpants type also includes a type in which these parts are formed of separate cloths and are integrated by sewing, a type in which the plurality of portions are formed of an integrated cloth, and a seamless type in which there is no seam between these portions.

The pelvic floor muscle supporting aid 10 has an annular part 20 and a pulling part 30. The annular part 20 is provided mainly on an inner surface of the crotch part 13 and depending on its size, also includes ranges adjacent to the crotch part 13 in the front body 11 and the back body 12. The annular part 20 is provided in the range mainly in the crotch part 13 so as to be situated at a position corresponding to the outer peripheral portion of the vaginal opening when the pelvic floor muscle supporting aid 10 is worn. The meaning of "the outer peripheral portion of the vaginal opening" includes not only a portion directly adjacent to the periphery of the vaginal opening but also the outer peripheral portion of the labia minora and the outer peripheral portion of the labia majora. In short, the annular part 20 only needs to be situated at a position where it surrounds the outer side of the vaginal opening and is capable of applying force in such a direction as to close the vaginal opening.

As illustrated in FIG. 2 and FIG. 3, the annular part 20 is, for example, elliptical in a plan view, and is provided such that its major axis direction is perpendicular to the width direction of the crotch part 13. The annular part 20 has left and side portions 21, 22 which are situated at positions that sandwich the vaginal opening and are between the vaginal opening and two leg openings 15, 15 in the worn state, and of substantially linear sides forming the left and right side portions 21, 22, end portions 21a, 22a close to the front body 11 are connected by a front portion 23, and end portions 21b, 22b close to the back body 12 is connected by a back portion 24.

It should be noted that, though the side portions 21, 22, the front portion 23, and the back portion 24 of the annular part 20 are all integrated in this embodiment, there may be a gap at each boundary between the side portions 21, 22 and the front and back portions 23, 24, or any of the side portions 21, 22, the front portion 23, and the back portion 24 may be discontinuous. Further, the side portions 21, 22 may be slightly curved. Further, the front portion 23 and the back portion 24 each may have a slightly curved shape as illustrated in the drawings, a substantially linear shape, a chevron shape with the vicinity of its middle protruding outward, or the like.

The pulling part 30 has a function of pulling the annular part 20 in at least a front direction or a back direction to narrow an interval between the left and right side portions 21, 22 of the annular part 20. In this embodiment, the pulling part 30 has front pulling parts 31 provided on ranges in the front body 11 and a back pulling part 32 provided on a range in the back body 12.

The number of the front pulling parts 31 is two in this embodiment, and they form a substantially V shape with their one-side ends 31a connected to the front portion 23 of the annular part 20 and with their other ends 31b extending toward the upper portion of the front body 11 to be apart from each other. This is intended for preventing the front pulling parts 31 from pressing the urethral meatus and so on.

The back pulling part 32 has one end 32a coupled with the vicinity of a middle portion 24a of the back portion 24 and the other end 32b extending toward an upper portion of the back body 12. That is, the single back pulling part 32 is provided along the vicinity of a middle portion of the back body 12 in terms of a width direction of the back body 12 (width direction of the pelvis). Note that, though the annular part 20 and the pulling part 30 (the front pulling parts 31 and the back pulling part 32) may be formed integrally of the same material as in this embodiment, they may be separately formed to be connected at the aforesaid portions.

As illustrated in FIG. 3, the front portion 23 of the annular part 20 is pulled in directions slightly fanning out to the left and right (the arrow A direction and the arrow B direction) by the two front pulling parts 31 forming the substantially V shape. Consequently, not only the vicinity of a middle portion of the front portion 23 but also the whole range of the front portion 23 is pulled in the aforesaid direction (the arrow C direction). On the other hand, as for the back portion 24, since the single back pulling part 32 is connected to the vicinity of its middle portion 24a, mainly the vicinity of the middle portion 24a is pulled toward the upper portion of the back body 12 (in the arrow D direction). When the vicinity of the middle portion 24a is pulled, the end portions 21b, 22b of the side portions 21, 22 situated at both ends of the back portion 24 are displaced in such directions as to narrow the interval therebetween (the arrow E direction and the arrow F direction). Consequently, the entire left and right side portions 21, 22 are displaced in such directions as to narrow the interval therebetween as indicated by the imaginary lines in FIG. 3. That is, the annular part 20 deforms such that its inner opening 20a becomes longer and narrower. When the side portions 21, 22 are thus displaced so as to narrow the interval therebetween, force to narrow the vaginal opening of the female genitals situated on an inner side of the side portions 21, 22 acts.

In this embodiment, the pelvic floor muscle supporting aid 10 is of the underpants type, and in a waist part 14 in the upper portions of the front body 11 and the back body 12, rubber is disposed to make the waist part 14 fit around the waist of a wearer. Instead of disposing the rubber, densely disposing elastic yarns on the waist part 14, coating the waist part 14 with synthetic resin, or the like can make only the waist part 14 higher in stretchability than the other portions of the front body 11 and the back body 12. It is also possible to fit the waist part 14 around the waist by separating the waist part 14 into segments and joining the segments with buttons, hooks, or the like. Further, if the front body 11 and the back body 12 themselves are at least partly formed of elastic yarns or coated with synthetic resin to have certain stretchability and fit the wearer owing to the stretchability, the rubber or the like need not be provided in the waist part 14. The front pulling parts 31 have the other ends 31b extending toward the upper portion of the front body 11 as described above. Preferably, the other ends 31b are connected to the waist part 14. Similarly, the other end 32b of the back pulling part 32 extends to the upper portion of the back body 12, and is preferably connected to the waist part 14. Since the waist part 14 is held around the waist when the pelvic floor muscle supporting aid 10 is worn, tensile force acts on the front pulling parts 31 and the back pulling part 32 in the upward direction (direction from the crotch part 13 toward the waist part 14). As a result, the front portion 23 and the back portion 24 of the annular part 20 which are connected to the ends 31a of the front pulling parts 31 and the end 32a of the back pulling part 32 respectively are pulled, so that the inner opening 20a of the annular part 20 deforms to become longer and narrower as described above.

Here, since the pelvic floor muscle supporting aid 10 of this embodiment is of the underpants type, the front body 11, the back body 12, and the crotch part 13 are formed of a material used for ordinary underwear, correction wear, and the like, typically a material having predetermined stretchability. However, in the front body 11, the back body 12, and the crotch part 13, on their portions corresponding to the aforesaid annular part 20 and pulling part 30, the force which starts from the waist part 14 to pull them upward is applied at the time of the wearing. Therefore, for example, the portions corresponding to the annular part 20 and the pulling part 30 can be formed to be lower in stretchability along the planar direction (pulling direction) than the other portions, or the portions corresponding to the annular part 20 and the pulling part 30 can be formed to be high in elastic restoring force along the planar direction (pulling direction). Specific examples of adoptable means for the above include: coating the portions corresponding to the annular part 20 and the pulling part 30 with resin to make these portions low in stretchability; forming only these portions of a different material relatively low in stretchability or a different material high in elastic restoring force and joining these portions with the other portions by sewing or by overlapping these portions on parts of adjacent portions and pasting them together by fusion or the like; and stacking a different material low in stretchability or a different material high in elastic restoring force on these portions and joining them by sewing, fusion, or the like. In the case where the material different from that of the front body 11, the back body 12, and the crotch part 13 is joined by sewing or the like, this material may be any of woven fabric, paper, synthetic resin, and the like, but is preferably a soft material that gives less discomfort even when in contact with the female genitals and skin.

Further, the annular part 20 preferably has a three-dimensional shape with at least part thereof, preferably the side portions 21, 22, bulging in the thickness direction. With this shape, the annular part 20 easily abuts on the outer peripheral portion of the vaginal opening, so that the force of biasing the vaginal opening in the closing direction by the annular part 20 easily acts. The annular part 20 may bulge in an outward direction, but preferably bulges inward, that is, in such a direction as to come into contact with the female genitals. A means for thus bulging the annular part 20 can be, for example, to stack a different material relatively lower in stretchability than the other portions, or the like on the portion corresponding to the annular part 20 as described above. The different material may be any of woven fabric, paper, synthetic resin, and so on and its kind is not limited as long as it is a soft material similarly to the above. Further, the material itself of the portion forming the annular part 20 disposed mainly on the crotch part 13 can be worked into a three-dimensional bulging shape. Note that, in the case where the annular part 20 at least partly bulges, its bulging height is not limited, but is preferably within a range of about 0.5 mm to about 20 mm and more preferably within a range of 1 mm to 5 mm in order to give less feeling of something foreign to the wearer, though different depending on the flexibility of the material and also depending on the bulging method, that is, depending on whether to bulge the material itself of the crotch part 13 or to stack the other material.

The operation of the pelvic floor muscle supporting aid 10 of this embodiment will be described. Since the pelvic floor muscle supporting aid 10 of this embodiment is of the underpants type, the wearer wears it by putting the legs into the leg openings 15, 15 in the same manner as he/she wears ordinary underpants. At this time, the pelvic floor muscle supporting aid 10 of this embodiment may be worn as innermost wear which directly comes into contact with the skin, or after ordinary underwear is worn, may be worn thereon. In either case, when the pelvic floor muscle supporting aid 10 of this embodiment is worn, the side portions 21, 22 of the annular part 20 are situated on the outer sides of the vaginal opening of the wearer, and at the same time, the front pulling parts 31 and the back pulling part 32 are pulled toward the waist part 14. Consequently, the front portion 23 and the back portion 24 of the annular part 20 are pulled in opposite directions (the arrow C direction and the arrow D direction in FIG. 3). As a result, the force to cause the annular part 20 to press the outer peripheral portion of the vaginal opening upward first acts to support the pelvic floor muscles. Consequently, it is possible to resist the pressure applied to the vagina from above to prevent the expansion of the vagina caused by the pressure.

Further, the back pulling part 32 is connected only to the middle portion 24a of the back portion 24. Accordingly, when the front portion 23 and the back portion 24 of the annular part 20 are pulled in the opposite directions (the arrow C direction and the arrow D direction in FIG. 3), the two side portions 21, 22 sandwiching the inner opening 20a of the annular part 20 try to be displaced in the directions in which they approach each other (the arrow E direction and the arrow F direction in FIG. 3). As a result, the forces act in such directions as to close the wearer's vaginal opening, which is corresponding to the side portions 21, 22, from the outer sides of the vaginal opening.

In short, according to this embodiment, owing to the annular part 20, the force to press the outer peripheral portion of the vaginal opening of the wearer upward to support the pelvic floor muscles and the forces in such directions as to close the vaginal opening act simultaneously. The forces to close the vaginal opening act to retain the pelvic organs which have not slipped out from the vaginal opening, in the vagina by pressing. Therefore, the pelvic floor muscle supporting aid 10 of this embodiment operates to support the pelvic floor muscles to return them into the normal positions and at the same time is expected to have a high effect of preventing the pelvic organ prolapse. Further, since pressing the vaginal opening upward while closing it, the pelvic floor muscle supporting aid 10 can provide an effect similar to that of pelvic floor muscle exercise, further can contribute to an improvement in the exercise effect of the pelvic floor muscle exercise, and has high effects of preventing and curing urine leakage, uncontrolled urination, and the like. Further, since the back portion 24 of the annular part 20 is situated at the position corresponding to the perineal region, it is also effective for preventing and curing lymphedema and varix occurring in the perineal region. Further, since the crotch wear article in the substantially flat plate shape as described in the aforesaid Patent Document 2 is not used, thigh sore which may be caused by such a crotch wear article as a foreign object does not occur.

Figure 4:
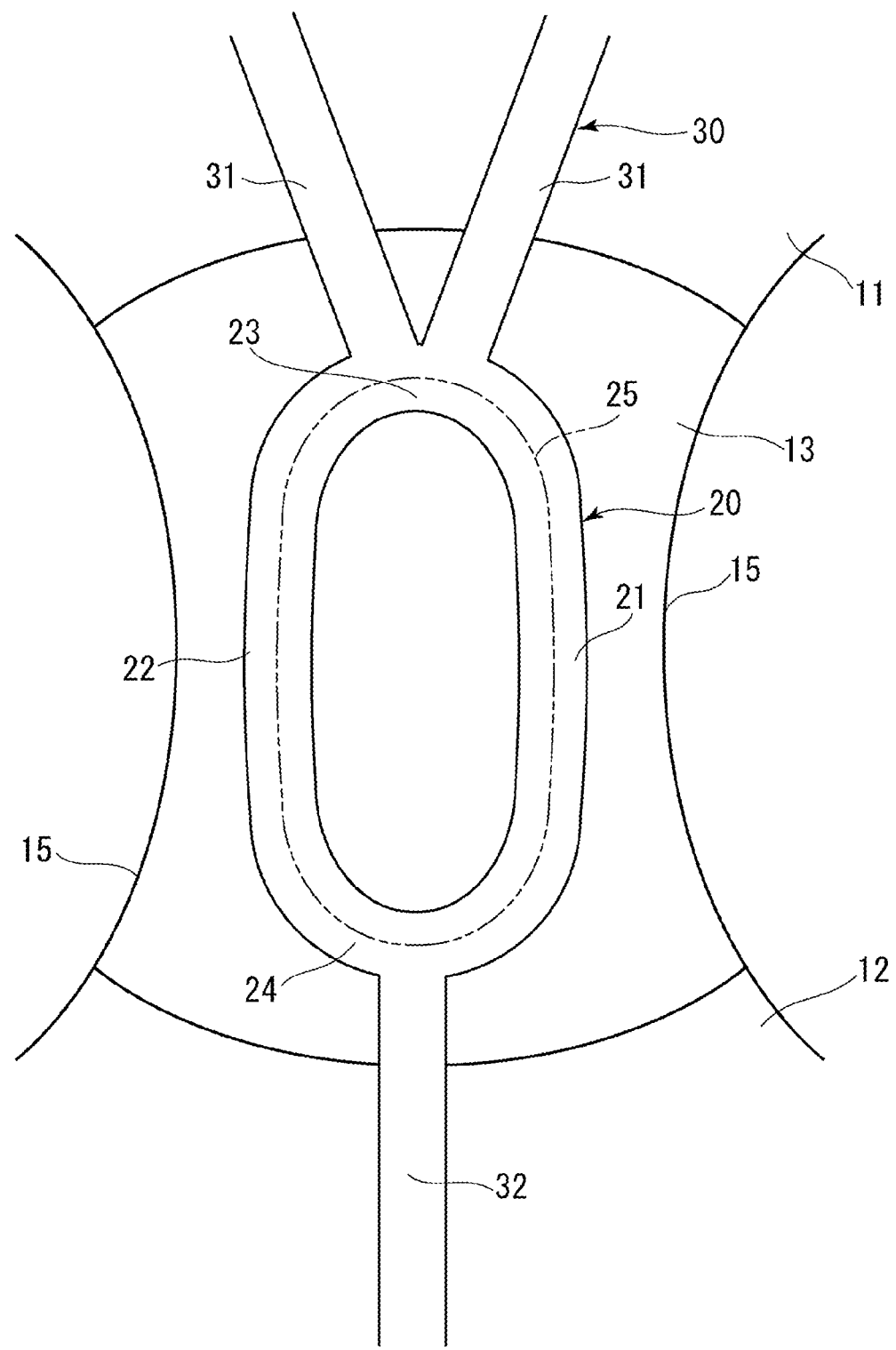
FIG. 4 is an explanatory view of the structure of an annular part of a pelvic floor muscle supporting aid according to another embodiment of the present invention and is a plan view of the annular part.

FIG. 4 is a plan view of the structure of an annular part 20 adopted in a pelvic floor muscle supporting aid 10 according to another embodiment of the present invention. In this embodiment, a middle pressing part 25 is provided as indicated by the imaginary line. The middle pressing part 25 is stacked on at least one side out of a front surface and a rear surface of the annular part 20 so as to be situated between side portions 21, 22 of the annular part 20 and is formed of a cloth or the like having a substantially elliptical outer periphery. The middle pressing part 25 only needs to be provided between the side portions 21, 22 of the annular part 20, and may have a narrower width than an interval between the side portions 21, 22, may be joined only to the vicinity of a front portion 23 and the vicinity of a back portion 24, and may have such a size as to have an interval from the side portions 21, 22. However, the wider its width, the softer its abutting feeling on the female genitals, which is more preferable. The middle pressing part 25 is formed of, for example, a material relatively lower in stretchability than the other portions of a front body 11 and a back body 12 similarly to the other portions (side portions 21, 22 and so on) of the annular part 20.

Therefore, in a worn state, when the front portion 23 and the back portion 24 of the annular part 20 are pulled in opposite directions (the arrow C direction and the arrow D direction in FIG. 3), the middle pressing part 25 tries to be displaced upward to press the female genitals. That is, since the middle pressing part 25 is disposed in the vicinity of the middle of the annular part 20, force acts in a direction such that it comes into contact with the vaginal opening or in a direction such that it presses the vaginal opening. This force together with the side portions 21, 22 acts as force to press the pelvic floor muscles upward, and further acts as force pressing up the pelvic organs which have fallen down to the vicinity of the vaginal opening or pressing the pelvic organs which have slipped out from the vaginal opening, in such a direction as to push the pelvic organs inside. Therefore, according to this embodiment, not only the pelvic floor muscles are supported and in addition, the side portions 21, 22 of the annular part 20 try to close the vaginal opening, but also the force to press the fallen pelvic organs can act more strongly owing to the middle pressing part 25.

Preferably, the middle pressing part 25 has a size such that its front portion and back portion are in contact with front pulling parts 31, 31 and a back pulling part 32 and it partly overlaps with the front pulling parts 31, 31 and the back pulling part 32. This makes the pulling forces of the front pulling parts 31, 31 and the back pulling part 32 directly act on the middle pressing part 25, making it possible to surely pull the middle pressing part 25. Further, at least part of the middle pressing part 25 preferably bulges. In this case, preferably at least one of its inner surface and outer surface, more preferably at least its inner surface, bulges to protrude toward the vaginal opening. This can more increase the force pressing the pelvic organs. A method to form this bulging portion may be any, and it is possible to form the bulging portion by stacking a flexible material in a plate shape, a semicircular shape, or the like formed of cloth, synthetic resin, paper, or the like on the middle pressing part 25 to increase its thickness, or by forming a slit in the middle pressing part 25 in advance and detachably attach a member formed in a semicircular shape or the like to the middle pressing part 25, with an end portion of the member inserted into the slit. Further, in the case where the annular part 20 formed mainly on the crotch part 13 is integrally formed with the crotch part 13 (or a crotch cloth provided inside) by resin coating or the like, a range surrounded by the annular part 20 can be the middle pressing part 25 as it is. In this case, stretchability or elastic restoring force is adjusted to differ among the annular part 20, the middle pressing part 25, the pulling part 30, the front body 11, the back body 12, and so on such that, when the annular part 20 is pulled, the pulling force also acts on the middle pressing part 25 to press the female genitals while the side portions 21, 22 are displaced to approach each other.

In the above-described embodiments, the two front pulling parts 31 composing the pulling part 30 are arranged in the substantially V shape, but as long as they can pull the front portion 23 of the annular part 20, their number, arrangement, shape, and so on are not limited. The back pulling part 32 only needs to be capable of pulling the vicinity of the middle portion 24a of the back portion 24 of the annular part 20. Typically, the single back pulling part 32 is provided as in the above-described embodiments, but the number of the back pulling parts 32 may be two or more as long as they can pull the vicinity of the middle portion 24a. For example, they can be disposed with their one-side ends connected to the vicinity of the middle portion 24a, to fan out in a substantially V shape as they go toward an upper portion of the back body 12. Further, the front pulling parts 31 and the back pulling part 32 may each have a bent portion or may be in a curved shape or the like instead of being linear. Further, the shape of the annular part 20 is not limited to the aforesaid shape as long as it can push the vaginal opening from left and right outer sides in the closing direction.

Further, in both of the above-described embodiments, the underpants-type pelvic floor muscle supporting aid 10 is shown, but instead of being of the underpants type including the front body 11 and the back body 12, the pelvic floor muscle supporting aid 10 may be structured to include, besides the annular part 20 and the pulling part 30, only a waist support member (not illustrated) supporting the pulling part 30 around the waist of a wearer. However, the aforesaid underpants type is easy to wear.

Further, as the material forming the front body 11 and the back body 12 of the pelvic floor muscle supporting aid 10, also usable is a cloth that does not get frayed from its cut edge, at whichever position it is cut. In this case, it is possible to provide the pelvic floor muscle supporting aid 10 in a state where the upper portions of the front body 11 and the back body 12 are at a high position, for example, around the navel so that the wearer can cut it at his/her desired position when he/she uses it. Similarly, it is possible to form, on leg openings 15 sides, leg insertion portions extending to the vicinity of the knees or the vicinity of the ankles so that the wearer can cut them at his/her desired position for length adjustment. Further, the pelvic floor muscle supporting aid 10 may be formed and provided as a bodysuit type so as to allow the wearer to cut it into his/her desired shape. By having an increased degree of freedom in shape and design, the pelvic floor muscle supporting aid 10 can suit the taste of the wearer to be more comfortable to wear. Further, cutoff lines (perforations) may be provided at, for example, several mm to several cm intervals in advance so that the wearer can cut it along the cutoff line at his/her desired position for length adjustment. Note that, as the cloth that does not easily get frayed, various conventionally known cloths are usable, and examples of the usable cloth include a knit structure of a non-elastic yarn and an elastic yarn running side by side, at least one of which is formed into closed stitches to prevent fraying from a cut edge as is disclosed in Japanese Patent Application Laid-open No. 2003-147618, an elastic cloth having a knit structure whose cut edge does not get frayed as is disclosed in Japanese Patent Application Laid-open No. 2009-215676, and one in which silicone resin is applied on a cloth formed of elastic yarns to prevent the fraying at its cut edge as is disclosed in Japanese Utility Model Registration No. 3123137.

The invention claimed is:

1. A pelvic floor muscle supporting aid, comprising: an annular part which has an inner opening area and is provided so as to be situated at a position corresponding to an outer peripheral portion of a vaginal opening when the pelvic floor muscle supporting aid is worn; and a pulling part which is coupled with the annular part and pulls the annular part in at least a front direction or a back direction of the vaginal opening to narrow an interval between left and right side portions of the annular part, the left and right side portions being situated on left and right of the vaginal opening, wherein the pelvic floor muscle supporting aid being of an underpants type having a front body, a back body, and a crotch part, wherein: the annular part is provided in a range including the crotch part; and the pulling part has a front pulling part provided on a range in the front body and a back pulling part provided on a range in the back body, wherein: the front pulling part includes a plurality of front pulling parts which are formed to fan out from a front portion of the annular part toward an upper portion of the front body; and the back pulling part has one end connected to a middle portion of a back portion of the annular part and has the other end extending toward an upper portion of the back body, and wherein the plurality of front pulling parts are two front pulling parts which form a substantially V shape, and the single back pulling part is provided along a widthwise middle portion of the back body, and wherein, in the front body, the back body, and the crotch part, portions corresponding to the annular part, the back pulling part, and the plurality of front pulling parts are formed to be lower in stretchability along a pulling direction than other portions.

2. The pelvic floor muscle supporting aid according to claim 1, further comprising a middle pressing part which is between the left and right side portions of the annular part and is pulled by the pulling part.

3. The pelvic floor muscle supporting aid according to claim 1, wherein the front body and the back body are each formed of a cloth that does not easily get frayed from a cut edge.

4. The pelvic floor muscle supporting aid according to claim 1, wherein the pulling part is directly connected to the annular part.

5. The pelvic floor muscle supporting aid according to claim 1, wherein the portions corresponding to the annular part, the back pulling part, and the plurality of front pulling parts are formed by resin coating; are formed by joining the portions with the other portions by sewing or by overlapping the portions on parts of adjacent portions and pasting them together by fusion, the portions of a different material relatively low in stretchability; or are formed by stacking a different material low in stretchability on the portions and joining them by sewing or fusion.

* * * * *